United States Patent [19]

Tamietto

[11] 4,186,133

[45] Jan. 29, 1980

[54] PROCESS FOR THE PREPARATION OF AN INDOLE-3-ACETOHYDROXAMIC ACID

[75] Inventor: Teresio Tamietto, Turin, Italy

[73] Assignee: Istituto Biologico Chemioterapico "ABC" S.p.A., Turin, Italy

[21] Appl. No.: 880,517

[22] Filed: Feb. 23, 1978

[51] Int. Cl.² .......................................... C07D 209/12
[52] U.S. Cl. .................. 260/326.13 R; 260/326.13 A
[58] Field of Search .............. 260/326.13 R, 326.13 A

[56] References Cited

U.S. PATENT DOCUMENTS 3,624,103  11/1971  De Martiis et al. ........ 260/326.13 R

OTHER PUBLICATIONS

Smith, "The Chemistry of Open Chain Organic Nitrogen Compounds", vol. II, p. 90, (1966).

Primary Examiner—Glennon H. Hollrah
Assistant Examiner—D. B. Springer
Attorney, Agent, or Firm—Sughrue, Rothwell, Mion, Zinn and Macpeak

[57] ABSTRACT

A process for the preparation of indole-3-acetohydroxamic acids having the formula:

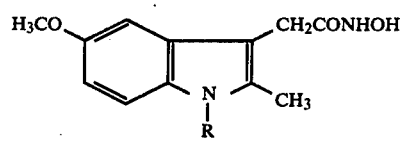

wherein R is a hydrogen atom or a p-chlorobenzoyl, benzyl or an allyl radical, in which the corresponding 2-methyl-5-methoxyindole-3-acetaldehyde is reacted with benzenesulfohydroxylamine in the presence of aqueous sodium hydroxide at from 0° C. to 4° C. at a pH less than 8, to form the sodium salt of the required acid. The required acid is liberated by the addition of hydrochloric acid and precipitated by the addition of water. The required acid in which R is a hydrogen atom may alternatively be prepared by debenzoylation of the acid in which R is the p-chlorobenzoyl radical.

14 Claims, No Drawings

PROCESS FOR THE PREPARATION OF AN INDOLE-3-ACETOHYDROXAMIC ACID

The present invention relates to the preparation of certain indole-3-acetohydroxamic acids, having the formula:

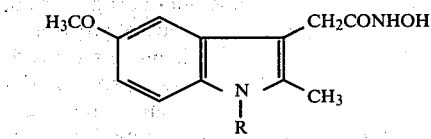

in which R may be a hydrogen atom or one of the following radicals:

p-chlorobenzoyl; 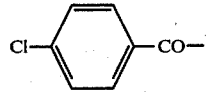

benzyl; 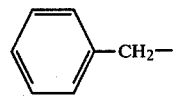

allyl; CH₂=CH—CH₂— 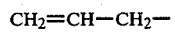

These acids are described in our U.S. Pat. No. 3,624,103 and have excellent anti-inflammatory, analgesic, and antipyretic activity.

The process of preparation described in the aforesaid U.S. patent is laborious, and does not give very satisfactory yields. The main object of the present invention is, therefore, to provide a simpler process for their preparation which can give high yields.

According to the present invention there is provided a process for the preparation of an indole-3-acetohydroxamic acid having the formula:

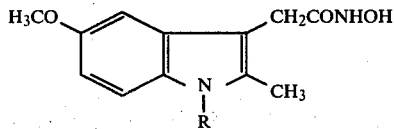

wherein R is a p-chlorobenzoyl, benzyl or an allyl radical or a hydrogen atom, characterised by the operations of:

(a) preparing a solution of a corresponding aldehyde having the formula:

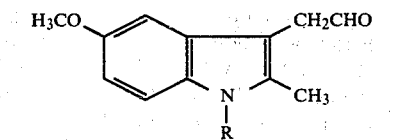

wherein R has the same signification as above and of benzenesulphohydroxylamine, that is:

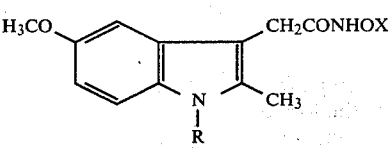

in an inert, as hereinafter defined, organic solvent, miscible with water;

(b) adding an aqueous solution of an alkali metal hydroxide having a strength of at least 1.5 N to the said solution kept under agitation at a temperature of from 0° C. to 8° C. to induce the reaction of the said aldehyde (II) and the said hydroxylamine (III) to form the corresponding alkali metal salt of the required indole-3-acetohydroxamic acid that is:

$$H_3CO\text{—indole—}CH_2CONHOX \quad (IV)$$

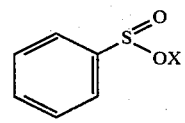

wherein R has the same signification as above and X is the alkali metal of the said alkali metal hydroxide, and the alkali metal salt of benzene sulphinic acid, that is:

(V)

wherein X has the same signification as above, the molar quantity of alkali metal hydroxide added being not substantially greater than the molar quantity of the said hydroxylamine dissolved in stage (a);

(c) liberating the indole-3-acetohydroxamic acid (I) from its salt formed in stage (b) by the addition of a water-soluble acid; and (d) precipitating the indole-3-acetohydroxamic acid (I) from solution by the addition of water.

In stage (a), by inert solvent is meant a solvent which is inert to the aldehyde II, the hydroxylamine III, the alkali added in stage (b) and to the reaction products of stage (b), and also to the acid added in stage (c) and to the required acid (I) under the reaction conditions of the respective stage. Thus, for example, neither alcoholic solvents nor acetone would be suitable. The solvents chosen are preferably also not harmful to personnel carrying out the process of the invention and hence the preferred solvents are dimethylsulphoxide (DMSO), dimethylformamide (DMFA), dioxan and tetrahydrofuran (THF). The solvent does not need to be anhydrous and in fact, at the reaction temperature, DMSO and dioxan would be solid if a small quantity of water were not added; the quantity of water should not exceed about 15% by weight of the organic solvent, however, since otherwise the solubility of the aldehyde (II) would be restricted.

The quantity of the said aldehyde (II) and of the said hydroxylamine (III) dissolved in stage (a) is preferably in the ratio 1 mole aldehyde (II):2 moles hydroxylamine (III): a greater proportion of the hydroxylamine produces no harmful affects but is not beneficial.

The strength of the aqueous alkali, preferably sodium hydroxide, used in stage (b) is not less than 1.5 N as at lower strengths too much water would be introduced into the reaction medium. The addition of the aqueous alkali and the agitation in stage (b) are preferably carried out in such a way that the pH in the reaction medium does not exceed a value of 8, since at higher pH values degradation products are formed, with consequent diminution in yield of the required product. The strength of the aqueous alkali used in stage (b) is preferably from 2 N to 4 N and in preferred embodiments is 2 N, since at pH values higher than 4 N there is a risk of exceeding pH 8 in the zone in which the alkali is added into the reaction medium, even with vigorous agitation. With the use of aqueous 2 N alkali the execution of stage (b) is extremely easy and sure; it suffices to effect the addition slowly and with moderate agitation.

In order to promote complete reaction of the aldehyde (II) with the hydroxylamine (III) the molar quantity of aqueous alkali added in stage (b) is preferably substantially equal to the molar quantity of the hydroxylamine used in stage (a); an excess of alkali over this amount leads to the formation of degradation products.

The reagent temperature in stage (b) is preferably from 0° C. to 4° C.

After the addition of the aqueous alkali the reaction mixture is preferably maintained under agitation, at the designated temperature for a period of time sufficient to allow the reaction to reach completion; for example, the reaction should certainly be complete after a period of one hour, but the time required may be determined by the change of colour of the reaction medium due to the using up of the aldehyde (II).

Upon completion of the reaction, the reaction products contained in the solution consist essentially of the alkali metal salts of the acid I and of benzenesulphinic acid.

In order to achieve complete liberation of the indole-3-acetohydroxamic acid (I) in stage (c), one equivalent of a water-soluble acid is preferably added for each mole of aldehyde (II) dissolved in stage (a). It is found that the acid reacts preferentially with the salt of the acid (I), leaving the sulphinic acid salt practically intact.

In stage (c) any one of a large number of water-soluble organic or mineral acids may be used such as, for example, hydrohalic, sulphuric, nitric, phosphoric, percholoric, formic, acetic, propionic, citric, tartaric and many other acids. The preferred acid, as in many other processes, is hydrochloric acid.

The reaction mass is preferably maintained under cooling in stage (c) even though the upper limit of 8° C. is not as critical as in stage (b).

The acid used in stage (c) is preferably not too dilute so as to avoid the introduction of sufficient water into the reaction medium to induce precipitation of the indole-3-acetohydroxamic acid (I) at this point. Preferably the strength of the acid added is at least 2 N.

The acid may be added as rapidly as desired since the reaction is practically instantaneous.

In the subsequent stage (d), the water used is preferably pre-cooled, advantageously to 0° C.–5° C. In order to produce practically complete precipitation of the acid (I), at least one volume of water is needed for each volume of solution obtained from stage (c); preferably about 2 volumes are used.

Since a small portion of the benzenesulphinic acid salt (V) tends to precipitate together with the acid (I), it is advisable to keep the mass under agitation for some minutes in order to re-dissolve the particles of sulphinate.

The precipitated acid (I) can be separated by filtration and then washed with water and dried. In order to eliminate any possible impurities which are insoluble in water the dried precipitate can be washed again, for example, with benzene or with chloroform.

If the process according to the invention is carried out in the preferred manner, it is found that yields of 75% or more of the theoretical yield are given.

Although the acid (I) in which R is a hydrogen atom, that is, 2-methyl-5-methoxyindole-3-acetohydroxamic acid, may be prepared directly from 2-methyl-5-methoxyindole-3-acetaldehyde by the process described above, in a preferred embodiment of the invention, this acid is prepared by first preparing 1-(p-chlorobenzoyl)-2-methyl-5-methoxyindole-3-acetohydroxamic acid, (formula I in which R is the p-chlorobenzoyl radical) by the above process, separating the acid from the solution obtained in step (d), and converting the acid to 2-methyl-5-methoxyindole-3-acetohydroxamic acid by debenzoylation.

The debenzoylation may be carried out by treatment with an aqueous, alcoholic, aqueous-alcoholic or aqueous-acetonic solution of an alkali metal hydroxide with subsequent precipitation of 2-methyl-5-methoxyindole-3-acetohydroxamic acid by treatment with a water-soluble acid.

Two embodiments of the invention will now be more particularly described, by way of example.

EXAMPLE 1

Preparation of 1-(p-chlorobenzoyl)-2-methyl-5-methoxyindole-3-acetohydroxamic acid The aldehyde used in this process is the 1-(p-chlorobenzoyl)-2-methyl-5-methoxyindole-3-acetaldehyde:

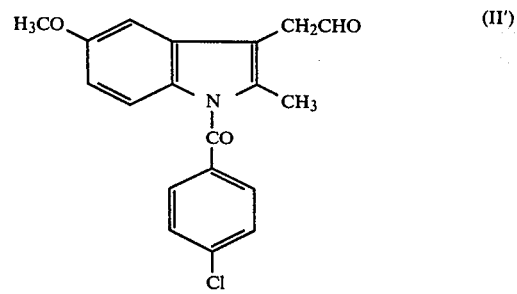

described, for example, in J. Med. Chem. 16,176,1973 and having when recrystallised from tert-butanol, a melting point of 120°–123° C.

4 mM (0.693g) of benzenesulphohydroxylamine and 2 mM (0.680g) of the aldehyde (II') are dissolved in a mixture consisting of 20 ml of DMSO and 2 ml of water, in a glass flask fitted with an agitator and a thermometer. A straw-yellow coloured solution is produced which is cooled by immersion of the flask in an ice/water mixture. When the temperature has stabilised at 0° C., 4 mEq of an aqueous 2 N solution of sodium hydroxide (NaOH) are added, drop by drop, under vigorous agitation. The solution in the flask takes on a brick-red colour. Cooling, under agitation, is continued for about one hour, and at least until the solution in the flask has reassumed the straw-yellow colour.

At this point 2 mEq of 2 N hydrochloric acid (analytically pure HCl) are added, agitation being continued.

The volume of the solution in the flask at this instant is about 25 ml. To this volume is added 50 ml of water, previously cooled to about 0° C., and agitation is continued for a further 2 minutes. The solution is filtered through a suction filter and a micro-crystalline precipitate of straw-yellow colour is collected. The precipitate is washed several times with water and then dried. The dry precipitate is shaken for several minutes in 8 ml of benzene to remove any unreacted aldehyde (II'), and any possible benzenesulphinic acid which may have been present. Finally, the solution is filtered through a Buchner funnel.

0.595 g of product are obtained, corresponding to a yield of about 80% of the theoretical. The product, checked by TLC (Thin-layer chromatography-plates—Merck DC Kieselgel 60 F$_{254}$ 0.25 mm, eluent-benzene:dioxan 80:40), consists of the desired 1-(p-chlorobenzoyl)-2-methyl-5-methoxyindole-3-acetohydroxamic acid which is practically pure, with traces of the original aldehyde. These latter are eliminated by means of recrystallation from hot dioxan (or from a 1:5 DMFA:acetone mixture) M.p.=182° C.-184° C. (dec.).

Elementary analysis for C$_{19}$H$_{17}$ClN$_2$O$_4$: % calculated: C, 61.21; H, 4.60; N, 7.51; Cl, 9.61. % Found: C, 61.26; H, 4.58; N, 7.46; Cl, 9.70.

The NMR and IR spectra are characteristic of the said 1-(p-chlorobenzoyl)-2-methyl-5-methoxyindole-3-acetohydroxamic acid, when prepared according to the U.S. patent referred to above,

EXAMPLE 2

Preparation of 2-methyl-5-methoxyindole-3-acetohydroxamic acid 4 mM (1.49 g) of 1-(p-chlorobenzoyl)-2-methyl-5-methoxyindole-3-acetohydroxamic acid prepared as in Example 1 are suspended in 20 ml of water at ambient temperature, in a 100 ml beaker. If desired, methanol, ethanol, acetone or mixtures of these with water, may be used instead of water. To the suspension, kept under agitation, there are added 8 ml of an aqueous 2 N solution of sodium hydroxide (16 mM). Within a period of 15-20 minutes the solid phase is observed to dissolve with formation of a clear liquid of straw-yellow colour. Agitation is continued for an hour after which 8.2 ml of aqueous 2 N hydrochloric acid are added. After a further 5 minutes of agitation, the precipitate which has formed is collected on a filter, washed repeatedly with water until the chlorides have disappeared (test with AgNO$_3$) and finally dried under vacuum.

The residue (1.45 g) consists of the desired acid and of p-chlorobenzoic acid in the proportions 6:4. In order to eliminate the p-chlorobenzoic acid, the said residue is suspended in 11.6 ml of dioxan at ambient temperature and shaken for 5-10 minutes.

Note: The volume of dioxan to be used is calculated on the ratio of 2 ml per 100 mg of p-chlorobenzoic acid to be removed.

The suspension is filtered and the residue is washed on the filter with 2-3 ml of dioxan. The residue consists of the desired 2-methyl-5-methoxyindole-3-acetohydroxamic acid. From the filtrate there separate spontaneously, in the course of 30-40 minutes, further white crystals of this acid, which are recovered by filtration, washed with 1-2 ml of dioxan and added to the previous residue. M.p. 172° C.-174° C. Total average yield 700-750 mg corresponding to 75%-80% of the theoretical.

Elementary analysis for C$_{12}$H$_{14}$N$_2$O$_3$: %C, 61.60 (calc. 61.52); %H, 5.90 (calc. 6.02); %N, 11.91 (calc. 11.96),
and the NMR spectrum, confirms that this is 2-methyl-5-methoxyindole-3-acetohydroxamic acid.

What is claimed is:

1. A process for the preparation of an indole-3-acetohydroxamic acid having the formula:

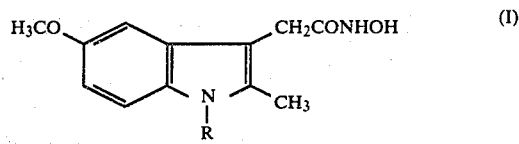

in which R is selected from: the p-chlorobenzoyl radical; benzyl radical; allyl radical; and a hydrogen atom, the process comprising the following sequence of steps:

(a) preparing a solution of a corresponding aldehyde having the formula:

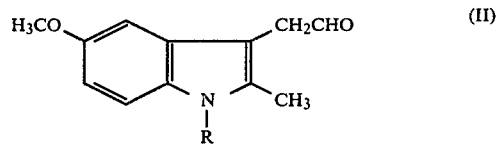

wherein R has the same signification as above and of benzenesulfohydroxylamine, that is:

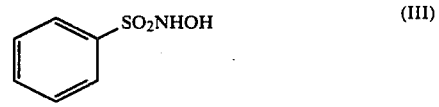

in an organic solvent, miscible with water;

(b) adding an aqueous solution of an alkali metal hydroxide having a strength of at least 1.5 N to the said solution kept at a pH value not exceeding 8 and kept under agitation at a temperature of from 0° C. to 8° C. to induce the reaction of the said aldehyde and the said hydroxylamine to form the corresponding alkali metal salts of the required indole-3-acetohydroxamic acid and of benzenesulphinic acid and recovering the indole-3-acetohydroxamic acid salt the molar quantity of alkali metal hydroxide added being not substantially greater than the molar quantity of said hydroxylamine dissolved in stage (a);

(c) liberating said indole-3-acetohydroxamic acid from its salt recovered from stage (b) by the addition of a water-soluble acid; and (d) precipitating said indole-3-acetohydroxamic acid by addition of water to the solution obtained in step (c), said organic solvent used in stage (a) being inert to said aldehyde, said benzenehydroxylamine, said aqueous alkali metal hydroxide and said alkali metal salts of said indole-3-acetohydroxamic acid and benzenesulphinic acid under said reaction conditions of stage (b) and to said acid added in stage (c) and said indole-3-acetohydroxamic acid and said organic solvent being selected from the group consisting of dimethyl sulfoxide, dime ylformamide, dioxan and tetrahydrofuran.

2. The process of claim 1, wherein said aldehyde and said benzenesulfohydroxylamine are dissolved in the solvent in stage (a) in a molar ratio of 1:2.

3. The process of claim 1, wherein said solvent is selected from dimethylsulfoxide and dioxan and contains water in a proportion not exceeding 15% by weight of said solvent.

4. The process of claim 1, wherein the molar quantity of said alkali metal hydroxide added in stage (b) is substantially equal to the molar quantity of said hydroxylamine dissolved in stage (a).

5. The process of claim 1, wherein said addition of aqueous alkali metal hydroxide and said agitation in stage (b) are carried out in such a manner that the pH in the reaction medium does not exceed a value of 8.

6. The process of claim 1, wherein the strength of said aqueous alkali metal hydroxide is from 2 N to 4 N.

7. The process of claim 6, wherein the strength of said aqueous alkali metal hydroxide is 2 N.

8. The process of claim 1, wherein said alkali metal hydroxide is sodium hydroxide.

9. The process of claim 1, wherein said temperature in stage (b) is from 0° C. to 4° C.

10. The process of claim 1, wherein the reaction medium in stage (b) is maintained under agitation at the designated temperature for a period of up to one hour after the addition of said alkali metal hydroxide, and at least until the reaction has reached completion.

11. The process of claim 1, wherein in stage (c) one equivalent of said water-soluble acid is added for each mole of said aldehyde dissolved in stage (a).

12. The process of claim 1, wherein said acid added in stage (c) has a strength of at least 2 N.

13. The process of claim 1, wherein said acid added in stage (c) is hydrochloric acid.

14. The process of claim 1, wherein at least one volume of water, precooled to from 0° C. to 5° C., is added in stage (d) for each volume of solution obtained from stage (c).

* * * * *